United States Patent [19]

Mukherjee

[11] Patent Number: 5,686,596
[45] Date of Patent: Nov. 11, 1997

[54] RECOMBINANT DNA ENCODING HUMAN PEROXISOME PROLIFERATOR ACTIVATED RECEPTOR

[75] Inventor: Ranjan Mukherjee, San Diego, Calif.

[73] Assignee: Ligand Pharmaceuticals Incorporated, San Diego, Calif.

[21] Appl. No.: 459,287

[22] Filed: Jun. 2, 1995

Related U.S. Application Data

[63] Continuation of Ser. No. 143,215, Oct. 26, 1993, abandoned, which is a continuation-in-part of Ser. No. 141,500, Oct. 22, 1993, abandoned.

[51] Int. Cl.$^6$ .............................. C12P 21/06; C07K 1/00; C07K 17/00
[52] U.S. Cl. .................... 536/23.5; 435/69.1; 435/320.1; 530/350
[58] Field of Search ....................... 536/23.5; 435/69.1, 435/320.1; 530/350

[56] References Cited

FOREIGN PATENT DOCUMENTS 2269897  2/1994  United Kingdom .

OTHER PUBLICATIONS

Havel and Kane, "Drugs and Lipid Metabolism," *Ann. Rev. Pharmac.* 13:287–308 (1973).

Green, "Receptor–Mediated Mechanisms of Peroxisome Proliferators," *Biochemical Pharmacology* 43:393–401 (1992).

Issemann and Green, "Activation of a Member of the Steroid Hormone Receptor Superfamily by Peroxisome Proliferators," *Nature* 347:645–650 (1990).

Göttlicher et al., "Fatty acids activate a chimera of the clofibric acid–activated receptor and the glucocorticoid receptor," *Proc. Natl. Acad. Sci. USA* 89:4653–4657 (1992).

Dreyer et al., "Control of the Peroxisomal β–Oxidation Pathway by a Novel Family of Nuclear Hormone Receptors," *Cell* 68:879–887 (1992).

Schmidt et al, "Identification of a New Member of the Steroid Hormone Receptor Superfamily That Is Activated by a Peroxisome Proliferator and Fatty Acids," *Molecular Endocrinology* 6:1634–1641 (1992).

Sher et al., "cDNA Cloning, Chromosomal Mapping, and Functional Characterization of the Human Peroxisome Proliferation Activated Receptor," *Biochemistry* 32: 5598–5604 (1993).

*Primary Examiner*—Stephen Walsh
*Assistant Examiner*—Daryl A. Basham
*Attorney, Agent, or Firm*—Lyon & Lyon LLP

[57] ABSTRACT

A human peroxisome proliferation activated receptor gene is purified from the environment in which it naturally occurs, and preferably provided within an expression vector.

5 Claims, 2 Drawing Sheets

```
ATGGTGGACA CGGAAAGCCC ACTCTGCCCC CTCTCCCCAC TCGAGGCCGG CGATCTAGAG AGCCCGTTAT CTGAAGAGTT CCTGCAAGAA ATGGGAAACA
 M  V  D  T  E  S  P  L  C  P  L  S  P  L  E  A  G  D  L  E  S  P  L  S  E  E  F  L  Q  E  M  G  N  I

TCCAAGAGAT TTCGCAATCC ATCGGCGAGG ATAGTTCTGG AAGCTTTGGC CCCTCCTCTG GTGACTTATC CGGCAGGTCC GACGAGTCTC CCAGTGGAGC ATTGAACATC
 Q  E  I  S  Q  S  I  G  E  D  S  S  G  S  F  G  F  T  E  Y  Q  Y  L  G  S  C  P  G  S  D  G  S  V

CATCACGGAC ACGCTTTCAC CAGCTTCCGA CCCTCCTCTG GTGACTTATC CGGCAGGTCC GACGAGTCTC CCAGTGGAGC ATTGAACATC
 I  T  D  T  L  S  P  A  S  S  P  S  S  V  T  Y  P  V  V  P  G  S  V  D  E  S  P  S  G  A  L  N  I

GAATGTAGAA TCTGCGGGGA CAAGGCCTCA GGCTATCATT ACGGAGTCCA GGCTGTGAA GGCTGCAAG CGACTCAAGC
 E  C  R  I  C  G  D  K  A  S  G  Y  H  Y  G  V  H  A  C  E  G  C  K  G  F  F  R  R  T  I  R  L  K  L

TGGTGTATGA CAAGTGCGAC CGCAGCTGCA AGATCCAGAA AAAGAACAGA AACAAATGCC AGTATTGTCG AATTCTTACC TGTGAACATG ACATAGAAGA TTCTGAAACT
 V  Y  D  K  C  D  R  S  C  K  I  Q  K  N  R  N  K  C  Q  Y  C  R  F  H  K  C  L  S  V  G  M  S

ACACAACGCG ATTCGTTTTG GACAATGTGA AAGCTGAGAA ACTTGAAGAA CTTCAACATG AACAAGGTCA AAGCCCGGGT CATCCTCTCA GGAAAGGCCA
 H  N  A  I  R  F  G  R  M  P  R  S  E  K  A  K  L  K  A  E  I  L  T  C  E  H  D  I  E  D  S  E  T

GCAGATCTCA AATCCTGGC CAAGAGAATC TACGAGGCT ATACATGATA TGGAGACACT GTGCACGTCA GTGGTGACCG TCACGGAGCT GCCAAGGCCA TCCCAGGCTT CGCAAACTTG
 A  D  L  K  S  L  A  K  R  I  Y  E  A  Y  L  K  N  F  N  M  K  V  K  A  R  V  I  L  S  G  K  A  S

GTAACAATGC ACCTTTTGTC CGCATCTTTC ACTGCTGCCA GTGCACGTCA GTGGTGACCG TCACGGAGCT GCCAAGGCCA TCCCAGGCTT CGCAAACTTG
 N  N  P  P  F  V  I  H  D  M  E  T  L  C  M  A  E  K  T  L  V  A  K  N  G  I  Q  N  K  E

GGCGGAGGTC CGCATCTTTC ACTGCTGCCA GTGCACGTCA GTGGTGACCG TCACGGAGCT GCCAAGGCCA TCCCAGGCTT CGCAAACTTG
 A  E  V  R  I  F  H  C  C  Q  C  T  S  V  E  T  V  T  E  L  T  E  F  A  X  A  I  P  G  F  A  N  L

GACCTGAACG ATCAAGTGAC ATTGCTAAAA CGTGAATTCC TAAAAAGCCT TCGTAAAACG AAGGAAACCG TTCTGTGATA TCATGGAACC CAAGTTTGAT AGTTCAATGC
 D  L  N  D  Q  V  T  L  L  K  Y  G  V  Y  E  A  I  F  A  M  L  S  S  V  M  N  K  D  G  M  L  V  A  Y

ATGGAAATGG GTTTATAACT CCTGAATTCC TTTTGTGGCT ATATCTCCCT GCTATCATTT GCTGTGGAGA TCGTCCTGGC CTTCTAAACG TAGGACACAT TGAAAAAATG
 G  N  G  F  I  T  R  E  F  L  K  S  L  R  K  P  F  C  D  I  M  E  P  K  F  D  F  A  M  K  F  N  A

ACTGGAACTG GATGACAGTG ATATCTCCCT TTTTGTGGCT ATATCTCCCT GCTATCATTT GCTGTGGAGA TCGTCCTGGC CTTCTAAACG TAGGACACAT TGAAAAAATG
 L  E  L  D  D  S  D  I  S  L  F  V  A  A  I  I  C  G  D  R  P  G  L  L  N  V  G  H  I  E  K  M

CAGGAGGGTA TTGTACATGT GCTCAGACTC CACCTGCAGA GCAACCACCC CGACGATATC TTTCTCTTCC CAAAACTTCT TCAAAAAATG GCAGACCTCC
 Q  E  G  I  V  H  V  L  R  L  H  L  Q  S  N  H  P  D  D  I  F  L  F  P  K  L  L  Q  K  M  A  D  L  R

GGCGACTGGT GACGCAGTCA GCGCAGCTGG TGCAGATCAT CAAGAAGACG GAGTCGGATG CAGTGCACTC GTGCCACTGA CAGGAGATCT ACAGGGACAT
 Q  L  V  T  E  H  A  Q  L  V  Q  I  I  K  K  T  E  S  D  A  A  L  H  P  L  L  Q  E  I  Y  R  D  M

GTACTGA
 Y
```

Fig. 1 mPPAR versus hPPAR1 Formated Alignment

```
mPPAR   MVDTESPICP LSPLEAQDLE SPLSEEFLQE MGNIQEISQS IGEESSGSFG FADYQYLGSC PGSEGSVITD TLSPASSPSS VSQPVIPAST DESPGSALNI  100
mPPAR1  MVDTESPLCP LSPLEAGDLE SPLSEEFLQE MGNIQEISQS IGEDSSGSFG FTEYQYLGSC PGSDGSVITD TLSPASSPSS VTYPMPDST  DESPGSALNI  100 mPPAR   ECRICGDKAS GYHYGVHACE GCKGFFRRIO RLKLVYDKCD RSCKIQKKNR NKCQYCRFHK CLSVGMSHNA IRFGRMPRSE KAKLKAEILT CEHDLKDSET  200
mPPAR1  ECRICGDKAS GYHYGVHACE GCKGFFRRIO RLKLVYDKCD RSCKIQKKNR NKCQYCRFHK CLSVGMSHNA IRFGRMPRSE KAKLKAEILT CEHDIEDSET  200 mPPAR   ADLKSLQKRI EAYLKNFNM  NKVKARVILA GKTISNNPPFV IHDMETLCMA EKTLVAKMVA NGVEDKEAEV RFFHCCQCVS VETVTELTEF AKAIPGFANL  300
mPPAR1  ADLKSLNKRI YEAYLKNFNM NKVKARVILS GKASNNPPFV  IHDMETLCMA EKTLVAKLVA NGIQNKEAEV RIFHCCQQTS VETVTELTEF AKAIPGFANL  300 mPPAR   DLNDQVTLLK YGVYEATFIM LSSLMNKDGM LIAYGNGFIT REFLKN RKP  FCDIMEPKFD FAMKFNALEL DDSDISLFVA AIICCGDRPG LLNIGYIEKL  400
mPPAR1  DLNDQVTLLK YGVYEAIFAM LSSMNKDGM  LMAYGNGFIT REFLKS RKP  FCDIMEPKFD FAMKFNALEL DDSDISLFVA AIICCGDRPG LLNMGHIEKM  400 mPPAR   QEGIVHVLKL HLQSNHPDDT FLFPKLLQKM MDLRQLVTEH AQLMQIKKT  ESDAALHPLL QEIYRDMY-                                      468
mPPAR1  QEGIVHVLPL HLQSNHPDDI FLFPKLLQKM ADLRQLVTEH AQLQIIKKT  ESDAALHPLL QEIYRDMYX                                      469
```

Fig. 2

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 1407 base pairs
( B ) TYPE: nucleic acid
( C ) STRANDEDNESS: single
( D ) TOPOLOGY: linear ( i i ) SEQUENCE DESCRIPTION: SEQ ID NO: 1:

```
ATG GTG GAC ACG GAA AGC CCA CTC TGC CCC CTC TCC CCA CTC GAG GCC      48
Met Val Asp Thr Glu Ser Pro Leu Cys Pro Leu Ser Pro Leu Glu Ala
              5                  10                  15

GGC GAT CTA GAG AGC CCG TTA TCT GAA GAG TTC CTG CAA GAA ATG GGA      96
Gly Asp Leu Glu Ser Pro Leu Ser Glu Glu Phe Leu Gln Glu Met Gly
             20                  25                  30

AAC ATC CAA GAG ATT TCG CAA TCC ATC GGC GAG GAT AGT TCT GGA AGC     144
Asn Ile Gln Glu Ile Ser Gln Ser Ile Gly Glu Asp Ser Ser Gly Ser
             35                  40                  45
```

| | | | | | | | | | | | | | | | | |
|---|---|---|---|---|---|---|---|---|---|---|---|---|---|---|---|---|
| TTT | GGC | TTT | ACG | GAA | TAC | CAG | TAT | TTA | GGA | AGC | TGT | CCT | GGC | TCA | GAT | 192 |
| Phe | Gly | Phe | Thr | Glu | Tyr | Gln | Tyr | Leu | Gly | Ser | Cys | Pro | Gly | Ser | Asp | |
| | 50 | | | | 55 | | | | | 60 | | | | | | |
| GGC | TCG | GTC | ATC | ACG | GAC | ACG | CTT | TCA | CCA | GCT | TCG | AGC | CCC | TCC | TCG | 240 |
| Gly | Ser | Val | Ile | Thr | Asp | Thr | Leu | Ser | Pro | Ala | Ser | Ser | Pro | Ser | Ser | |
| 65 | | | | 70 | | | | | 75 | | | | | | 80 | |
| GTG | ACT | TAT | CCT | GTG | GTC | CCC | GGC | AGC | GTG | GAC | GAG | TCT | CCC | AGT | GGA | 288 |
| Val | Thr | Tyr | Pro | Val | Val | Pro | Gly | Ser | Val | Asp | Glu | Ser | Pro | Ser | Gly | |
| | | | | 85 | | | | | 90 | | | | | 95 | | |
| GCA | TTG | AAC | ATC | GAA | TGT | AGA | ATC | TGC | GGG | GAC | AAG | GCC | TCA | GGC | TAT | 336 |
| Ala | Leu | Asn | Ile | Glu | Cys | Arg | Ile | Cys | Gly | Asp | Lys | Ala | Ser | Gly | Tyr | |
| | | | 100 | | | | | 105 | | | | | 110 | | | |
| CAT | TAC | GGA | GTC | CAC | GCG | TGT | GAA | GGC | TGC | AAG | GGC | TTC | TTT | CGG | CGA | 384 |
| His | Tyr | Gly | Val | His | Ala | Cys | Glu | Gly | Cys | Lys | Gly | Phe | Phe | Arg | Arg | |
| | | 115 | | | | | 120 | | | | | 125 | | | | |
| ACG | ATT | CGA | CTC | AAG | CTG | GTG | TAT | GAC | AAG | TGC | GAC | CGC | AGC | TGC | AAG | 432 |
| Thr | Ile | Arg | Leu | Lys | Leu | Val | Tyr | Asp | Lys | Cys | Asp | Arg | Ser | Cys | Lys | |
| | 130 | | | | | 135 | | | | | 140 | | | | | |
| ATC | CAG | AAA | AAG | AAC | AGT | TTC | AAA | TGC | CAG | TAT | TGT | CGA | TTT | CAC | AAG | 480 |
| Ile | Gln | Lys | Lys | Asn | Arg | Asn | Lys | Cys | Gln | Tyr | Cys | Arg | Phe | His | Lys | |
| 145 | | | | | 150 | | | | | 155 | | | | | 160 | |
| TGC | CTT | TCT | GTC | GGG | ATG | TCA | CAC | AAC | GCG | ATT | CGT | TTT | GGA | CGA | ATG | 528 |
| Cys | Leu | Ser | Val | Gly | Met | Ser | His | Asn | Ala | Ile | Arg | Phe | Gly | Arg | Met | |
| | | | | 165 | | | | | 170 | | | | | 175 | | |
| CCA | AGA | TCT | GAG | AAA | GCA | AAA | CTG | AAA | GCA | GAA | ATT | CTT | ACC | TGT | GAA | 576 |
| Pro | Arg | Ser | Glu | Lys | Ala | Lys | Leu | Lys | Ala | Glu | Ile | Leu | Thr | Cys | Glu | |
| | | | 180 | | | | | 185 | | | | | 190 | | | |
| CAT | GAC | ATA | GAA | GAT | TCT | GAA | ACT | GCA | GAT | CTC | AAA | TCT | CTG | GCC | AAG | 624 |
| His | Asp | Ile | Glu | Asp | Ser | Glu | Thr | Ala | Asp | Leu | Lys | Ser | Leu | Ala | Lys | |
| | | 195 | | | | | 200 | | | | | 205 | | | | |
| AGA | ATC | TAC | GAG | GCC | TAC | TTG | AAG | AAC | TTC | AAC | ATG | AAC | AAG | GTC | AAA | 672 |
| Arg | Ile | Tyr | Glu | Ala | Tyr | Leu | Lys | Asn | Phe | Asn | Met | Asn | Lys | Val | Lys | |
| | 210 | | | | | 215 | | | | | 220 | | | | | |
| GCC | CGG | GTC | ATC | CTC | TCA | GGA | AAG | GCC | AGT | AAC | AAT | CCA | CCT | TTT | GTC | 720 |
| Ala | Arg | Val | Ile | Leu | Ser | Gly | Lys | Ala | Ser | Asn | Asn | Pro | Pro | Phe | Val | |
| 225 | | | | | 230 | | | | | 235 | | | | | 240 | |
| ATA | CAT | GAT | ATG | GAG | ACA | CTG | TGT | ATG | GCT | GAG | AAG | ACG | CTG | GTG | GCC | 768 |
| Ile | His | Asp | Met | Glu | Thr | Leu | Cys | Met | Ala | Glu | Lys | Thr | Leu | Val | Ala | |
| | | | | 245 | | | | | 250 | | | | | 255 | | |
| AAG | CTG | GTG | GCC | AAT | GGC | ATC | CAG | AAC | AAG | GAG | GCG | GAG | GTC | CGC | ATC | 816 |
| Lys | Leu | Val | Ala | Asn | Gly | Ile | Gln | Asn | Lys | Glu | Ala | Glu | Val | Arg | Ile | |
| | | | 260 | | | | | 265 | | | | | 270 | | | |
| TTT | CAC | TCG | TGC | CAG | TGC | ACG | TCA | GTG | GTG | ACC | GTC | ACG | GAG | CTC | ACG | 864 |
| Phe | His | Cys | Cys | Gln | Cys | Thr | Ser | Val | Val | Thr | Val | Thr | Glu | Leu | Thr | |
| | | 275 | | | | | 280 | | | | | 285 | | | | |
| GAA | TTC | GCC | AAG | GCC | ATC | CCA | GGC | TTC | GCA | AAC | TTG | GAC | CTG | AAC | GAT | 912 |
| Glu | Phe | Ala | Lys | Ala | Ile | Pro | Gly | Phe | Ala | Asn | Leu | Asp | Leu | Asn | Asp | |
| | 290 | | | | | 295 | | | | | 300 | | | | | |
| CAA | GTG | ACA | TTG | CTA | AAA | TAC | GGA | GTT | TAT | GAG | GCC | ATA | TTC | GCC | ATG | 960 |
| Gln | Val | Thr | Leu | Leu | Lys | Tyr | Gly | Val | Tyr | Glu | Ala | Ile | Phe | Ala | Met | |
| 305 | | | | | 310 | | | | | 315 | | | | | 320 | |
| CTG | TCT | TCT | GTG | ATG | AAC | AAA | GAC | GGG | ATG | CTG | GTA | GCG | TAT | GGA | AAT | 1008 |
| Leu | Ser | Ser | Val | Met | Asn | Lys | Asp | Gly | Met | Leu | Val | Ala | Tyr | Gly | Asn | |
| | | | | 325 | | | | | 330 | | | | | 335 | | |
| GGG | TTT | ATA | ACT | CGT | GAA | TTC | CTA | AAA | AGC | CTA | AGG | AAA | CCG | TTC | TGT | 1056 |
| Gly | Phe | Ile | Thr | Arg | Glu | Phe | Leu | Lys | Ser | Leu | Arg | Lys | Pro | Phe | Cys | |
| | | | 340 | | | | | 345 | | | | | 350 | | | |
| GAT | ATC | ATG | GAA | CCC | AAG | TTT | GAT | TTT | GCC | ATG | AAG | TTC | AAT | GCA | CTG | 1104 |
| Asp | Ile | Met | Glu | Pro | Lys | Phe | Asp | Phe | Ala | Met | Lys | Phe | Asn | Ala | Leu | |
| | | 355 | | | | | 360 | | | | | 365 | | | | |

```
GAA CTG GAT GAC AGT GAT ATC TCC CTT TTT GTG GCT GCT ATC ATT TGC    1152
Glu Leu Asp Asp Ser Asp Ile Ser Leu Phe Val Ala Ala Ile Ile Cys
    370             375                 380

TGT GGA GAT CGT CCT GGC CTT CTA AAC GTA GGA CAC ATT GAA AAA ATG    1200
Cys Gly Asp Arg Pro Gly Leu Leu Asn Val Gly His Ile Glu Lys Met
385             390                 395                         400

CAG GAG GGT ATT GTA CAT GTG CTC AGA CTC CAC CTG CAG AGC AAC CAC    1248
Gln Glu Gly Ile Val His Val Leu Arg Leu His Leu Gln Ser Asn His
                405                 410                 415

CCG GAC GAT ATC TTT CTC TTC CCA AAA CTT CTT CAA AAA ATG GCA GAC    1296
Pro Asp Asp Ile Phe Leu Phe Pro Lys Leu Leu Gln Lys Met Ala Asp
            420                 425                 430

CTC CGG CAG CTG GTG ACG GAG CAT GCG CAG CTG GTG CAG ATC ATC AAG    1344
Leu Arg Gln Leu Val Thr Glu His Ala Gln Leu Val Gln Ile Ile Lys
        435                 440                 445

AAG ACG GAG TCG GAT CGT GCG CTG CAC CCG CTA CTG CAG GAG ATC TAC    1392
Lys Thr Glu Ser Asp Ala Ala Leu His Pro Leu Leu Gln Glu Ile Tyr
    450                 455                 460

AGG GAC ATG TAC TGA                                                1407
Arg Asp Met Tyr
465         468
```

( 2 ) INFORMATION FOR SEQ ID NO: 2:

( i ) SEQUENCE CHARACTERISTICS:
        ( A ) LENGTH: 468 amino acids
        ( B ) TYPE: amino acid
        ( D ) TOPOLOGY: linear ( i i ) SEQUENCE DESCRIPTION: SEQ ID NO: 2:

```
Met Val Asp Thr Glu Ser Pro Leu Cys Pro Leu Ser Pro Leu Glu Ala
                5               10                  15

Gly Asp Leu Glu Ser Pro Leu Ser Glu Glu Phe Leu Gln Glu Met Gly
            20                  25                  30

Asn Ile Gln Glu Ile Ser Gln Ser Ile Gly Glu Asp Ser Ser Gly Ser
                35                  40                  45

Phe Gly Phe Thr Glu Tyr Gln Tyr Leu Gly Ser Cys Pro Gly Ser Asp
    50                  55                  60

Gly Ser Val Ile Thr Asp Thr Leu Ser Pro Ala Ser Ser Pro Ser Ser
65                  70                  75                  80

Val Thr Tyr Pro Val Val Pro Gly Ser Val Asp Glu Ser Pro Ser Gly
                85                  90                  95

Ala Leu Asn Ile Glu Cys Arg Ile Cys Gly Asp Lys Ala Ser Gly Tyr
                100                 105                 110

His Tyr Gly Val His Ala Cys Glu Gly Cys Lys Gly Phe Phe Arg Arg
            115                 120                 125

Thr Ile Arg Leu Lys Leu Val Tyr Asp Lys Cys Asp Arg Ser Cys Lys
130                 135                 140

Ile Gln Lys Lys Asn Arg Asn Lys Cys Gln Tyr Cys Arg Phe His Lys
145                 150                 155                 160

Cys Leu Ser Val Gly Met Ser His Asn Ala Ile Arg Phe Gly Arg Met
                165                 170                 175

Pro Arg Ser Glu Lys Ala Lys Leu Lys Ala Glu Ile Leu Thr Cys Glu
            180                 185                 190

His Asp Ile Glu Asp Ser Glu Thr Ala Asp Leu Lys Ser Leu Ala Lys
        195                 200                 205

Arg Ile Tyr Glu Ala Tyr Leu Lys Asn Phe Asn Met Asn Lys Val Lys
    210                 215                 220
```

```
Ala  Arg  Val  Ile  Leu  Ser  Gly  Lys  Ala  Ser  Asn  Asn  Pro  Pro  Phe  Val
225                      230                 235                     240

Ile  His  Asp  Met  Glu  Thr  Leu  Cys  Met  Ala  Glu  Lys  Thr  Leu  Val  Ala
                    245                 250                     255

Lys  Leu  Val  Ala  Asn  Gly  Ile  Gln  Asn  Lys  Glu  Ala  Glu  Val  Arg  Ile
               260                 265                     270

Phe  His  Cys  Cys  Gln  Cys  Thr  Ser  Val  Glu  Thr  Val  Thr  Glu  Leu  Thr
          275                      280                     285

Glu  Phe  Ala  Lys  Ala  Ile  Pro  Gly  Phe  Ala  Asn  Leu  Asp  Leu  Asn  Asp
     290                      295                 300

Gln  Val  Thr  Leu  Leu  Lys  Tyr  Gly  Val  Tyr  Glu  Ala  Ile  Phe  Ala  Met
305                      310                 315                     320

Leu  Ser  Ser  Val  Met  Asn  Lys  Asp  Gly  Met  Leu  Val  Ala  Tyr  Gly  Asn
                    325                 330                     335

Gly  Phe  Ile  Thr  Arg  Glu  Phe  Leu  Lys  Ser  Leu  Arg  Lys  Pro  Phe  Cys
               340                 345                     350

Asp  Ile  Met  Glu  Pro  Lys  Phe  Asp  Phe  Ala  Met  Lys  Phe  Asn  Ala  Leu
          355                      360                 365

Glu  Leu  Asp  Asp  Ser  Asp  Ile  Ser  Leu  Phe  Val  Ala  Ala  Ile  Ile  Cys
370                      375                 380

Cys  Gly  Asp  Arg  Pro  Gly  Leu  Leu  Asn  Val  Gly  His  Ile  Glu  Lys  Met
385                 390                 395                     400

Gln  Glu  Gly  Ile  Val  His  Val  Leu  Arg  Leu  His  Leu  Gln  Ser  Asn  His
               405                 410                     415

Pro  Asp  Asp  Ile  Phe  Leu  Phe  Pro  Lys  Leu  Leu  Gln  Lys  Met  Ala  Asp
          420                      425                 430

Leu  Arg  Gln  Leu  Val  Thr  Glu  His  Ala  Gln  Leu  Val  Gln  Ile  Ile  Lys
     435                      440                 445

Lys  Thr  Glu  Ser  Asp  Ala  Ala  Leu  His  Pro  Leu  Leu  Gln  Glu  Ile  Tyr
     450                      455                 460

Arg  Asp  Met  Tyr
465            468
```

( 2 ) INFORMATION FOR SEQ ID NO: 3:

( i ) SEQUENCE CHARACTERISTICS:
      ( A ) LENGTH: 468 amino acids
      ( B ) TYPE: amino acid
      ( D ) TOPOLOGY: linear ( i i ) SEQUENCE DESCRIPTION: SEQ ID NO: 3:

```
Met  Val  Asp  Thr  Glu  Ser  Pro  Ile  Cys  Pro  Leu  Ser  Pro  Leu  Glu  Ala
                    5                   10                      15

Asp  Asp  Leu  Glu  Ser  Pro  Leu  Ser  Glu  Glu  Phe  Leu  Gln  Glu  Met  Gly
               20                  25                      30

Asn  Ile  Gln  Glu  Ile  Ser  Gln  Ser  Ile  Gly  Glu  Glu  Ser  Ser  Gly  Ser
          35                  40                      45

Phe  Gly  Phe  Ala  Asp  Tyr  Gln  Tyr  Leu  Gly  Ser  Cys  Pro  Gly  Ser  Glu
     50                  55                      60

Gly  Ser  Val  Ile  Thr  Asp  Thr  Leu  Ser  Pro  Arg  Ser  Ser  Pro  Ser  Ser
65                  70                      75                          80

Val  Ser  Cys  Pro  Val  Ile  Pro  Ala  Ser  Thr  Asp  Glu  Ser  Pro  Gly  Ser
               85                  90                      95

Ala  Leu  Asn  Ile  Glu  Cys  Arg  Ile  Cys  Gly  Asp  Lys  Ala  Ser  Gly  Tyr
          100                     105                     110
```

| | | | | | | | | | | | | | | |
|---|---|---|---|---|---|---|---|---|---|---|---|---|---|---|
| His | Tyr | Gly 115 | Val | His | Ala | Cys 120 | Glu | Gly | Cys | Lys | Gly 125 | Phe | Arg | Arg |
| Thr | Ile 130 | Arg | Leu | Lys | Leu | Val 135 | Tyr | Asp | Lys | Cys | Asp 140 | Arg | Ser | Cys | Lys |
| Ile 145 | Gln | Lys | Lys | Asn | Arg 150 | Asn | Lys | Cys | Gln | Tyr 155 | Cys | Arg | Phe | His | Lys 160 |
| Cys | Leu | Ser | Val | Gly 165 | Met | Ser | His | Asn | Ala 170 | Ile | Arg | Phe | Gly | Arg 175 | Met |
| Pro | Arg | Ser | Glu 180 | Lys | Ala | Lys | Leu | Lys 185 | Ala | Glu | Ile | Leu | Thr 190 | Cys | Glu |
| His | Asp | Leu 195 | Lys | Asp | Ser | Glu | Thr 200 | Ala | Asp | Leu | Lys | Ser 205 | Leu | Gly | Lys |
| Arg | Ile 210 | His | Glu | Ala | Tyr | Leu 215 | Lys | Asn | Phe | Asn | Met 220 | Asn | Lys | Val | Lys |
| Ala 225 | Arg | Val | Ile | Leu | Ala 230 | Gly | Lys | Thr | Ser | Asn 235 | Asn | Pro | Pro | Phe | Val 240 |
| Ile | His | Asp | Met | Glu 245 | Thr | Leu | Cys | Met | Ala 250 | Glu | Lys | Thr | Leu | Val 255 | Ala |
| Lys | Met | Val | Ala 260 | Asn | Gly | Val | Glu | Asp 265 | Lys | Glu | Ala | Glu | Val 270 | Arg | Phe |
| Phe | His | Cys 275 | Cys | Gln | Cys | Met | Ser 280 | Val | Glu | Thr | Val | Thr 285 | Glu | Leu | Thr |
| Glu | Phe 290 | Ala | Lys | Ala | Ile | Pro 295 | Gly | Phe | Ala | Asn | Leu 300 | Asp | Leu | Asn | Asp |
| Gln 305 | Val | Thr | Leu | Leu | Lys 310 | Tyr | Gly | Val | Tyr | Glu 315 | Ala | Ile | Phe | Thr | Met 320 |
| Leu | Ser | Ser | Leu | Met 325 | Asn | Lys | Asp | Gly | Met 330 | Leu | Ile | Ala | Tyr | Gly 335 | Asn |
| Gly | Phe | Ile | Thr 340 | Arg | Glu | Phe | Leu | Lys 345 | Asn | Leu | Arg | Lys | Pro 350 | Phe | Cys |
| Asp | Ile | Met 355 | Glu | Pro | Lys | Phe | Asp 360 | Phe | Ala | Met | Lys | Phe 365 | Asn | Ala | Leu |
| Glu | Leu | Asp 370 | Asp | Ser | Asp | Ile 375 | Ser | Leu | Phe | Val | Ala 380 | Ala | Ile | Ile | Cys |
| Cys 385 | Gly | Asp | Arg | Pro | Gly 390 | Leu | Leu | Asn | Ile | Gly 395 | Tyr | Ile | Glu | Lys | Leu 400 |
| Gln | Glu | Gly | Ile | Val 405 | His | Val | Leu | Lys | Leu 410 | His | Leu | Gln | Ser | Asn 415 | His |
| Pro | Asp | Asp | Thr 420 | Phe | Leu | Phe | Pro | Lys 425 | Leu | Leu | Gln | Lys | Met 430 | Val | Asp |
| Leu | Arg | Gln 435 | Leu | Val | Thr | Glu | His 440 | Ala | Gln | Leu | Val | Gln 445 | Val | Ile | Lys |
| Lys | Thr 450 | Glu | Ser | Asp | Ala | Ala 455 | Leu | His | Pro | Leu | Leu 460 | Gln | Glu | Ile | Tyr |
| Arg 465 | Asp | Met | Tyr 468 | | | | | | | | | | | | |

RECOMBINANT DNA ENCODING HUMAN PEROXISOME PROLIFERATOR ACTIVATED RECEPTOR

CROSS REFERENCE TO RELATED APPLICATION

This application is a continuation of application Ser. No. 08/143,215, filed Oct. 26, 1993, abandoned which is a Continuation in Part of Mukherjee, application Ser. No. 08/141,500 entitled "HUMAN PEROXISOME PROLIFERATOR ACTIVATED RECEPTOR", filed on Oct. 22, 1993 now abandoned.

FIELD OF THE INVENTION

This invention relates to the cloning and uses of a human peroxisome proliferator activated receptor.

BACKGROUND OF THE INVENTION

A peroxisome proliferator is an agent that induces peroxisomal proliferation. Peroxisome proliferators are a diverse group of chemicals which include unsaturated fatty acids, hypolipidemic drugs, herbicides, leukotriene antagonists, and plasticizers (for a review, see Green, S., 43 Biochem. Pharmacol. 393–400, 1992). Hypolipidemic drugs such as clofibrates have been found to lower triglycerides and cholesterol levels in plasma and to be beneficial in the prevention of ischaemic heart disease in individuals with elevated levels of cholesterol (Havel, R. J. and Kane, J. P., 13 Ann. Rev. Pharmac. 287–308, 1973). Therapeutic use of such drugs, however, is questioned because clofibrates are carcinogens in rats.

Peroxisome proliferator activated receptor (PPAR) is a member of the steroid receptor family. It is activated by peroxisome proliferators. Issemann and Green, 347 Nature 645, 1990, cloned a mouse peroxisome proliferator activated receptor (mPPAR) gene from a mouse liver complementary DNA (cDNA) library. Göttlicher et al., 89 Proc. Nat. Acad. Sci. USA 4653–4657, 1992, cloned a rat peroxisome proliferator activated receptor (rPPAR) gene from a rat liver cDNA library. PPARs from mouse and rat share 97% homology in amino acid sequence and a particularly well-conserved putative ligand-binding domain. Three members of the Xenopus nuclear hormone receptor superfamily have also been found to be structurally and functionally related to the mPPAR (Dreyer et al., 68 Cell 879–887, 1992).

Schmidt et al., 6 Molecular Endocrinology 1634–1641, 1992, cloned asteroid hormone receptor gene, NUC1, from a human osteosarcoma cell cDNA library. The homology between amino acid sequence of NUC1 and that of the mouse PPAR is only 62%. Thus, although it is clear that NUC1 is a member of the PPAR receptor group, it remains to be determined whether NUC1 is the human homolog of the mouse PPAR or a new member of the PPAR family.

Sher et al., 32 Biochemistry 5598–5604, 1993, cloned a human PPAR gene from a human liver cDNA library. This clone has 85% nucleotide sequence homology and 91% amino acid sequence homology with the mPPAR clone.

SUMMARY OF THE INVENTION

The present invention relates to the cloning of a human PPAR gene, hPPAR1. The protein encoded by hPPAR1 has 92% homology with the mouse PPAR. It is different from the human PPAR cloned by Sher et al., supra, at two locations in the amino acid sequence, i.e., amino acids 268 and 296.

The hPPAR1 clone can be used for the expression of large amounts of hPPAR1. This human PPAR clone is also useful for screening compounds for improved pharmacological profiles for the treatment of hyperlipidemia with higher potency, efficacy, and fewer side effects. Specifically, the human PPAR clone can be used to screen for compounds active as primary endogenous inducers of the human PPAR. In addition, it is useful for establishing the tissue specific expression pattern of human PPAR. For example, a Northern blot can be used to reveal tissue specific expression of the gene to aid treatment of diseases such as atherosclerosis.

Thus, in a first aspect, the invention features a purified nucleic acid encoding a human PPAR with the nucleotide base sequence shown in FIG. 1, and given as SEQ ID NO. 1. By purified nucleic acid is meant that the nucleic acid is separated from its natural environment and from other nucleic acids.

In a second aspect, the present invention features a vector containing the human PPAR gene. This vector may be used for multiplication of the human PPAR gene or expression of the human PPAR gene.

In a preferred embodiment, the vector is an expression vector. In one example, the expression vector is used to make a recombinant human PPAR nucleic acid, which can be used as a specific probe for DNA or RNA complementary to the human PPAR sequence. In another example, the expression vector is used to express human recombinant PPAR protein.

By vector is meant a plasmid or viral DNA molecule into which either a cDNA or a genomic DNA sequence is inserted.

By expression vector is meant a vector that directs protein synthesis from a promoter. In a preferred embodiment, either vector pBacPAK8 (Clontech) or vector pBacPAK9 (Clontech) is used to express the human PPAR in insect cells. In another preferred embodiment, vector pYES2 (Invitrogen) is used to express the human PPAR in yeast cells. In yet another preferred embodiment, pBKCMV (Stratagene) is used to express the human PPAR in mammalian cells.

By recombinant human PPAR is meant a non-naturally expressed human PPAR.

Other features and advantages of the invention will be apparent from the following description of the preferred embodiments thereof, and from the claims.

DESCRIPTION OF THE PREFERRED EMBODIMENTS BRIEF DESCRIPTION OF THE DRAWINGS

FIG. 1 is the nucleotide and amino acid sequence of hPPAR1 SEQ ID NO: 1 and 2; and FIG. 2 is a comparison of the amino acid sequences of hPPAR1 SEQ ID NO: 2 and the mouse PPAR SEQ ID NO: 3.

What follows is an example of the cloning of a human PPAR. Those of ordinary skill in the art will recognize that equivalent procedures can be readily used to isolate human PPAR from cDNA libraries or genomic libraries of other tissues than that exemplified below, namely the liver.

In general, the cloning of the human PPAR involved probing a human liver cell cDNA library with a labeled EcoRI-BglII fragment (nucleotides 450–909) of the rat PPAR (459 bases). The sequence of the probe is shown in G öttlicher et al. supra.

The recipes for buffers, mediums, and solutions in the following examples are given in J. Sambrook, E. F. Fritsch, and T. Maniatis, Molecular Cloning: A Laboratory Manual, 2 Ed., Cold Spring Harbor Laboratory Press, Cold Spring Harbor, N.Y., 1989.

EXAMPLE 1

Cloning of a human PPAR

A human PPARsubtype, hPPAR1, was cloned from a human liver 5'-stretch cDNA library (Clontech #HL1115a)

in lambda gt10 phages. C600-Hfl coli (Clontech) was grown overnight in LB broth supplemented with 0.2% maltose. A required amount of phage (corresponding to 2 million plaques) was mixed with 200 microliters of 10 mM MgCl₂/10 mM CaCl₂ and 1.5 milliliters of the overnight C600-Hfl coli and incubated at 37° C. for 30 minutes. Soft LB agarose was added at 48° C., mixed and poured onto prewarmed 22×22 cm rectangular LB agar plates and incubated overnight at 37° C.

Plaque lifts were performed by chilling the plates at 4° C. to harden the top agarose and prevent it from peeling, marking a nylon or nitrocellulose filter on the surface contacting the plaques, laying the filter on the surface without trapped air bubbles, and leaving it for about a minute. A number of asymmetric dots were inserted with Indian ink with a syringe and needle so that the ink soaked into the agar. The sheets were then peeled gently away, and laid plaque side up on two sheets of Whattman 3MM soaked in denaturing solution, and left for about 2 minutes. The sheets were then peeled away and immersed in a standard neutralizing solution for 5 minutes, immersed in 5× SSC, air dried, and baked at 80° C. under vacuum, for 2 hours.

The filters were prehybridized in 40% formamide, 5× SSC, 0.1% SDS, 1× Denhardt, and 100 ng/ml denatured salmon sperm DNA at 37°–42° C. for 1 hour. Labeled DNA probe (1 million cpm/ml) was denatured by heating at 100° C. for 10 minutes, chilled, and then added to the prehybridization solution, and hybridized at 37°–42° C. overnight. The filters were washed in 2× SSC and, 0.1% SDS at 42° C. or higher temperature.

Positive plaques were identified and purified by rescreening two more times. The probe was labeled by nick-translation.

Phage stocks were made by isolating and removing a well separated plaque with the narrow end of an autoclaved Pasteur pipette, immersing it in 1 ml of standard SM buffer, and adding a drop of chloroform. This was left for a few hours at room temperature (20° C.–24° C.) or overnight at 4° C., vortexed, and centrifuged.

The cDNA insert was amplified by polymerase chain reactions (PCR). 20 microliters of phage stock was used in 100 microliters of standard PCR reaction buffer, by adding all components except Polymerase. This mixture was heated to 99° C., and Vent DNA polymerase (Biolabs) was added to start the PCR cycles. The PCR conditions were 95° C. 1 minute, 72° C. 1 minute, 72° C. 3 minutes (1 minute per kilobase) for 30 cycles, 72° C. 5 minutes, and kept at 4° C. till further utilized.

The applicant isolated a clone from the cDNA library using an EcoR1-BglII fragment (nucleotides 450–909) of the rat PPAR (459 bases) as a probe and the hybridization conditions provided above. This clone was purified and its sequence defined. This sequence is shown in FIG. 1, and as SEQ. ID. NO. 1. FIG. 2 is a comparison of mPPAR and hPPAR1 amino acid sequences with those amino acids having identity between the two sequences enclosed in blocks.

EXAMPLE 2

Northern blot analysis

A human multiple tissue Northern blot was purchased from Clontech. Screening was done following the manufacturer's protocol. The blot was prehybridized in 5× SSPE, 10× Denhardt's solution, 100 µg/ml of freshly denatured salmon sperm DNA, 50% formamide and 2% SDS for 3 hours at 42° C. DNA from the EcoR1 site at position 1025 of the coding region to the end of the cloned gene was used as probe (see FIG. 1). This DNA was labeled by random priming, boiled and added at a concentration of 1 million cpm/ml of prehybridization solution. Hybridization was carried out for 13 hours at 42° C. The blot was then washed in 2× SSC, 0.05% SDS at room temperature followed by two washes in 0.1× SSC, 0.1% SDS at 50° C. and exposed to X-ray film.

A specific band of about 10 kilobase was observed in all tissues except the brain. Maximal expression was observed in skeletal muscle, followed by heart, placenta, pancreas, liver, kidney, and lung. The expression of hPPAR1 gene is therefore observed in tissues known to express PPARs in other species.

What is claimed is:

1. Purified nucleic acid comprising the nucleotide sequence shown in SEQ ID NO. 1.

2. A vector comprising said nucleic acid of claim 1.

3. A recombinant peroxisome proliferator activated receptor obtained by expressing the nucleic acid of claim 1.

4. A purified recombinant peroxisome proliferator activated receptor comprising the amino acid sequence shown in SEQ ID NO. 2.

5. Purified nucleic acid comprising a nucleotide sequence encoding the amino acid sequence shown in SEQ ID NO. 2.

* * * * *